US009346071B2

United States Patent
Davenport

(10) Patent No.: US 9,346,071 B2
(45) Date of Patent: May 24, 2016

(54) MULTI-PURPOSE SHOWERHEAD WITH WATER FLOSSING, EAR CLEANING AND TILE AND GROUT CLEANING MECHANISMS

(71) Applicant: Natalie Davenport, Neosho, MO (US)

(72) Inventor: Natalie Davenport, Neosho, MO (US)

( * ) Notice: Subject to any disclaimer, the term of this patent is extended or adjusted under 35 U.S.C. 154(b) by 0 days.

(21) Appl. No.: 14/514,564

(22) Filed: Oct. 15, 2014

(65) Prior Publication Data

US 2015/0102130 A1  Apr. 16, 2015

Related U.S. Application Data

(60) Provisional application No. 61/890,994, filed on Oct. 15, 2013.

(51) Int. Cl.
| | | |
|---|---|---|
| *A61C 17/02* | (2006.01) | |
| *A61C 17/028* | (2006.01) | |
| *A61C 17/032* | (2006.01) | |
| *B05B 1/08* | (2006.01) | |
| *B05B 1/16* | (2006.01) | |
| *B05B 1/18* | (2006.01) | |
| *B05B 15/00* | (2006.01) | |

(52) U.S. Cl.
CPC .............. *B05B 15/00* (2013.01); *A61C 17/0214* (2013.01); *B05B 1/16* (2013.01); *B05B 1/18* (2013.01)

(58) Field of Classification Search
CPC .... A61C 15/00; A61C 17/02; A61C 17/0202; A61C 17/0214; A61C 17/028; B05B 1/16; B05B 1/18; B05B 15/00; A61H 13/00; A61H 33/6021; A61H 33/6057; A47K 3/281
See application file for complete search history.

(56) References Cited

U.S. PATENT DOCUMENTS

| | | | | |
|---|---|---|---|---|
| 3,820,532 A | * | 6/1974 | Eberhardt | A61C 17/028 601/165 |
| 4,043,337 A | * | 8/1977 | Baugher | A61C 17/0214 601/162 |
| 4,564,005 A | * | 1/1986 | Marchand | A61C 17/028 601/165 |
| 5,070,553 A | * | 12/1991 | Chambers | E03C 1/06 239/390 |
| 5,241,714 A | * | 9/1993 | Barry | A47K 3/281 4/605 |
| 5,626,472 A | * | 5/1997 | Pennetta | A61C 17/0214 433/80 |
| 7,276,035 B2 | * | 10/2007 | Lu | A61C 17/0202 433/80 |

* cited by examiner

*Primary Examiner* — Darren W Gorman
(74) *Attorney, Agent, or Firm* — Bay State IP, LLC

(57) ABSTRACT

A multi-purpose showerhead to increase the ease and efficiency of personal hygiene. The back of the showerhead has a compartmental chamber which houses several multi-functional hygienic water tools of different colors or braille that can be personalized for each individual. The chamber also a tile and grout cleaner. The inside of showerhead with multi-functional hygienic water tools and the inside of the chamber are coated or made in an antibacterial substance. Each tool comprises a spring-activated rubber slide, which, when activated, slides whichever individual tool is required, out of the aperture and makes it available for use.

3 Claims, 4 Drawing Sheets

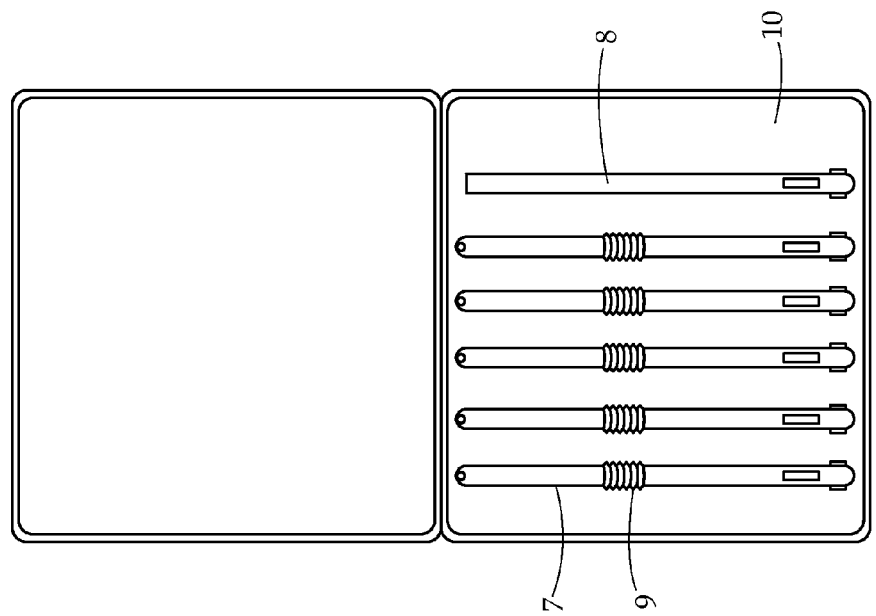
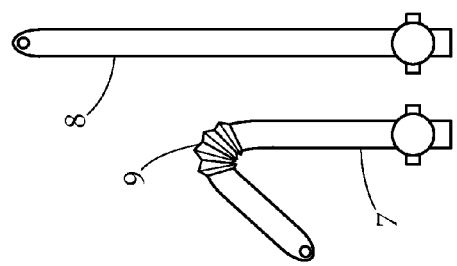
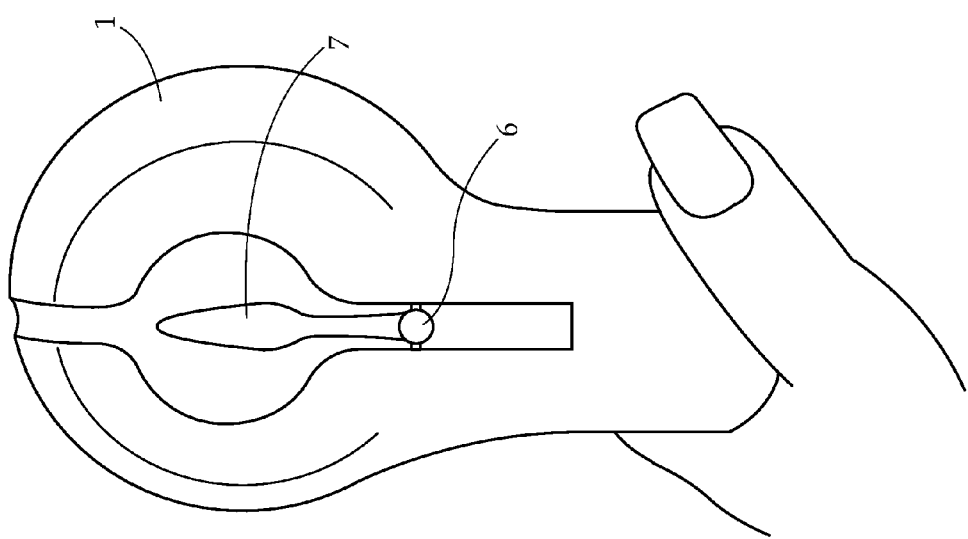
Fig. 8
Fig. 7
Fig. 6

MULTI-PURPOSE SHOWERHEAD WITH WATER FLOSSING, EAR CLEANING AND TILE AND GROUT CLEANING MECHANISMS

CROSS-REFERENCE TO RELATED APPLICATION

This application claims the benefit of and takes priority from U.S. Provisional App. No. 61/890,994 filed on Oct. 15, 2013, the contents of which are hereby incorporated by reference.

FIELD OF THE INVENTION

The present invention relates to a multi-purpose showerhead equipped with water flossing devices, ear cleaners, and tile and grout cleaners.

BACKGROUND OF THE INVENTION

Personal hygiene and its importance in medical health are constantly evolving. Knowing its role of stopping diseases and improving health it should be our role as people to find ways to make personal hygiene easier and less time consuming. Thousands of years ago the ancient Egyptians who, who showed a concern for personal hygiene, went as far as installing public bathing facilities in the tombs of the dead so they may start their next life off with proper hygiene. The ancient Greeks installed hot and cold water systems for bathing in their homes and bath houses and incorporated pumice stones, for scrubbing their bodies, into their hygienic routine. The tradition of maintain proper hygiene was continued by the Roman Empire, which was famous for the construction of many state-of-the-art public bathing facilities that dotted its vast Mediterranean empire.

In the modern era we place a premium on personal hygiene; teaching our children from an early age the importance of cleanliness. The modern emphasis on personal hygiene is pure and simple: Good personal hygiene kills germs and bacteria and helps prevent illness and the spread of disease.

The annals of history are full of examples of times when humans neglected personal hygiene, like the Black Death, which struck the medieval world with devastating consequences. Even today there are societies that do not have access to clean water supplies for bathing, showering, and oral hygiene and the presence of disease, tooth decay, and other associated health problems are rampant.

Water is required to conduct many forms of personal hygiene and is the most important nutrient and the most abundant substance in the human body. Water comprises about three quarters of the human mass and is a major component in every cell. Clean water is important to human health for many reasons. It's needed for energy in body as the ions help for electrical pathways for nerve functions. Water is needed to maintain everything in the body; it plays a part in physical and mental functions, and helps the body remove toxins. Water is a must for personal hygiene and the maintenance of all bodily functions.

A key part of personal hygiene is teeth cleaning. When trying to maintain a healthy smile and fresh breath regular preventative oral hygiene is pivotal. Without proper care, the teeth can decay quickly causing many health complications for the patient. Even though preventing cavities is a relatively simple process, it is still something many people struggle with.

To help prevent oral problems the most powerful tool is regularly brushing your teeth to remove dangerous plaque and food particles that damage the gums and teeth. Flossing is also important as it helps maintain healthy gums and it should be done at least once a day, where brushing should be done twice a day. There are currently two types of flossing. The first, and most widely used is the practice of using a small piece of string between the teeth, removing small particles of food and tarter that cannot be reached by a toothbrush. The other method of flossing is water flossing, where a device provides a water stream to clean around the teeth, removing small particles of food, biofilm, and tarter that cannot be reached by a typical toothbrush.

If a person isn't practicing good oral hygiene then they are opening the door to potentially dangerous oral problems that require invasive surgeries, medications, loss of teeth, and constant pain. Severe gum disease causes over one-third of adult tooth loss. Tooth decay is the most common disease on the planet. Over eighty percent of cavities occur inside pits and fissures on the chewing surfaces where brushing cannot reach food that is trapped after eating and the person's saliva or fluoride has no access to neutralize the acid and remineralize demineralized teeth, unlike the easy-to-reach surfaces, where the fewer cavities occur.

Once a person is diagnosed with an oral disease there are treatment options that should be considered and acted upon. Because every person is different and their disease symptoms may vary, the type of treatments can differ as well. There are four surgical treatment procedures that can be performed, to help the patient but it would be economically beneficial and healthier to just avoid developing the need for such procedures in the first place. Proactive care is the best course of action, as taking care of your teeth now will prevent dental problems in the future.

The use of string or water floss is an important element of oral hygiene since it removes plaque and decaying food stuck between teeth. This food decay and plaque cause irritation to the gums, causing, among other problems, bleeding gums. Acidic foods left on the teeth can also demineralize them and eventually causing cavities. The number of times a person flosses has been directly correlated to the development of cancer or stroke making it highly important to care for one's oral hygiene. The reason for this however is largely to do with a person's immune system. If bacteria are present in a person's mouth then their immune system will be constantly battling it to prevent further health problems. When an immune system is being taxed it elevates one's blood pressure allowing viruses a window of opportunity to attack and succeed. The mouth is the primary place where this is a problem because it is a warm and moist environment which is perfect for the spread of bacteria and due to the fact that the mouth offers a direct passage to the stomach through which bacteria and germs can pass through into the bloodstream. In short, should someone have a bad type of bacteria in their mouth it can easily travel into the stomach and result in a full blown illness that affects more than the mouth. Another reason that the oral cavity is a particularly vulnerable area is due to the range of things that are put into it. For example we lick our fingers after touching things, we wipe our mouths, and we eat food that is perhaps no longer that good for consumption.

Personal oral hygiene is important for other people's health as well as our own. When we cough or sneeze we broadcast the bacteria and germs in our mouths into the air and surrounding surfaces where others come into contact with them. While keeping a hand in front of one's mouth will help prevent the dispersion of bacteria from a cough or sneeze, it's better to avoid any bad bacteria in the mouth in the first place.

Unfortunately, keeping on top of oral hygiene is not a high priority for some, especially when it comes to flossing regularly. A major reason why many people do not floss is because they dislike the string floss because it is awkward, messy, or just difficult. There are however, alternatives to string flossing. You can floss with an electrical or battery powered water flossing device, but that too has some disadvantages.

Some of the disadvantages to the battery and electrical water flossing device include the fact that they take up on space on countertops so if a person does not have the counter space available the device has to be stored and taken out each time for usage, the devices collect dust, limited water supply, the reservoir has to be cleaned after use as it harbors mold and mildew, batteries have to be charged or replaced and are expensive, they have a very limited pressure because of the limited reservoir pumps break, pumps and lines hold water that is considered unclean, bathrooms can turn into a big mess because of splashing water that bounces back off teeth ends up all over the countertop and mirror, cords get tangled, water supply hose can get kinked, floors gets wet, tubes and hoses need to be replaced often, and can seals can leak.

Water flossing devices are an easier and more effective way to floss only having to be done once a day for approximately one minute. In a recent clinical study it was found that adding water flossing to a normal tooth brushing was fifty percent more effective method at cleaning teeth than string flossing was and that water flossing improved gum health eighty percent better than air flossing. A similar study looked at adolescents with fixed orthodontic equipment and showed that a water flossing devices with a special tip designed for orthodontics was 3.8 times more effective at removing plaque than string flossing and 5.8 times more effective than just a normal brushing routine.

A multi-purpose shower head with an oral dental water flossing devices will make it easier to floss with fewer steps and help promote better oral hygiene hereby improving one's health. Water flossing can also benefit some who struggle with dexterity challenges such as arthritis or muscular dystrophy. It can help promote children's health especially those who are unable to understand the proper way to string floss. The multi-purpose showerhead with a water flossing devices is a great improvement over other water flossing devices because there is no reservoir to refill, the water stream is continuous, and the water temperature can be adjusted without dumping the reservoir. The multi-purpose showerhead with its multi-functional hygienic water tools has been invented for cleaning the mouth and ears with precise water pressure that can be controlled via different attachments for comfort and various cleaning needs.

This new showerhead with its multifunction hygienic water tools has another added feature, it is a hand mounted shower unit that can be set in a cradle and allows it to act like a fixed showerhead with added versatility and flexible movement. It will also aid in cleaning the bathtub, feet, and other areas of the body because of the flexible movement. Also the tile and grout cleaning tip will let people have a high pressure stream with the option of pulses to clean grout without having to use harsh chemicals.

SUMMARY OF THE INVENTION

The present mechanism, illustrated herein, is clearly not anticipated, rendered obvious, or present in any of the prior art mechanisms, either alone or in any combination thereof. Therefore, it is the object of the present device, an installable multi-function shower head, is to promote personal hygiene on several levels by providing ashowerhead containing a multi-water flow pulsation system for a water flossing devices to clean one's ears and oral cavity.

An additional object of the instant apparatus is that the water flosser/ear cleaner will be described as a multi-functional hygienic water tool. Another objective of the current system is to provide a showerhead that also contains a water pulsation tile and grout cleaner. It is a further objective of the instant device that there are rubberized spring action mechanisms that cause the multi-functional hygienic water tools to come up through a small hole with cover when engaged. When one of the sliding mechanisms is engaged snapped into place it causes the water flow to move from shower head to the multi-functional hygienic water tool. The sliders may be manufactured with a curved designed for ease of handheld use and the sliders may also be colored or numbered with braille.

An additional objective of the present mechanism is that the multi-functional hygienic water tools and tile and grout cleaner all have separate compartments allowing the other multi-functional hygienic water tools to be kept from being exposed to germs. For further germ protection both the inside of the compartments and inside of the multi-functional hygienic water tools has been constructed with an antibacterial coating. Furthermore, the instant apparatus has the purpose ot place, at the bottom of compartment in base of handle, a small hole for drainage of water that may be on the multi-functional hygienic water tools when they are no longer in use. It is another intention of the current device that there is a second embodiment. In this embodiment there is one water flow with an attachment mechanism.

It is the intent of the second embodiment that there are several multi-functional hygienic water tools and a tile and grout cleaner, which can be attached to the water flow one at a time. All of the multi-functional hygienic water tools and the tile and grout cleaner are interchange and compatible with the attachment mechanism. Additionally, the multi-functional hygienic water tools and the tile and grout clear are different colors as well, as labeled with braille for easy identification. Further, for the purpose of germ prevention, the tools are housed in an antibacterial storage device when not in use.

An additional of both embodiments is that the showerhead handle contain a control panel with a series of buttons that enables the user to control the water pressure and pulsation. It is a further objective of both embodiments that immediately below the showerhead handle there is a twisting mechanism, allowing a person to twist it and switch the flow of water from the front of the showerhead to the back.

It is a further object of the instant system to introduce a removably attachable embodiment wherein the user is afforded the capability to install the instant control panel and system, including the multi-functional hygienic water tools and tile and grout cleaner and subsequently seamlessly detach the system from the installation point.

It is to be understood that the invention is not limited in its application to the details of its construction nor the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

These together, with the other objectives of the device, along with the various features of novelty, which characterize the apparatus, are pointed out with particularity in the claims annexed to and forming a part of this disclosure. For a better understanding of the mechanism, its operating advantages, and the specific objectives attained by its use, study of the accompanying drawings and descriptive matter, in which there are illustrations of the preferred embodiments, should be conducted.

BRIEF DESCRIPTION OF THE DRAWINGS

FIG. 6 is a view of the second embodiment of the device from the back of the showerhead.

FIG. 7 is a view of the detachable multi-functional hygienic water tools and tile and grout cleaner removed from the back of the invention in the second embodiment.

FIG. 8 is a view of the antibacterial storage compartment for the multi-functional hygienic water tools and the tile and grout cleaner of the second embodiment.

DETAILED DESCRIPTION OF THE INVENTION

Figure 2:
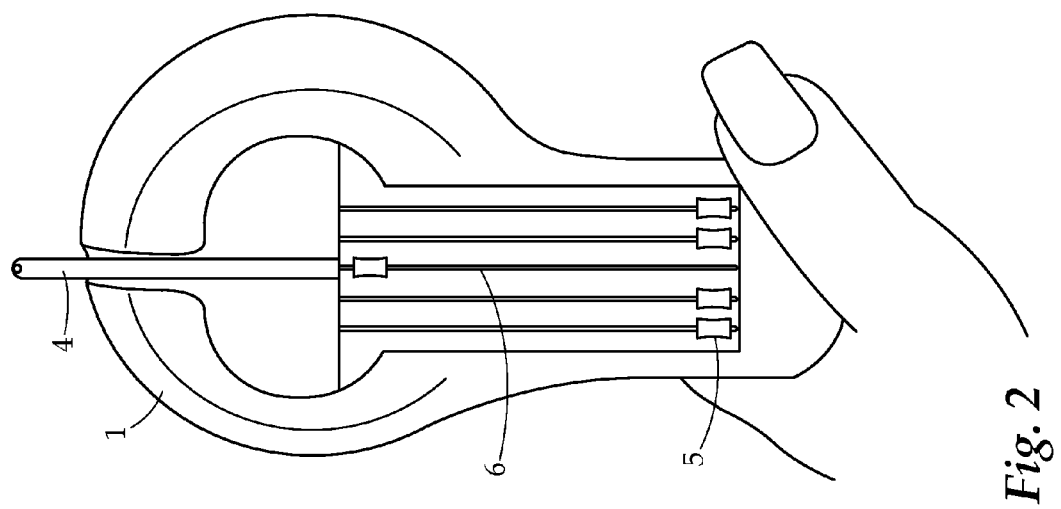
FIG. 2 is a backside view of the outside of invention showing how the multi-functional hygienic water tools and tile and grout cleaner are contained and slide in and out.
Figure 1:
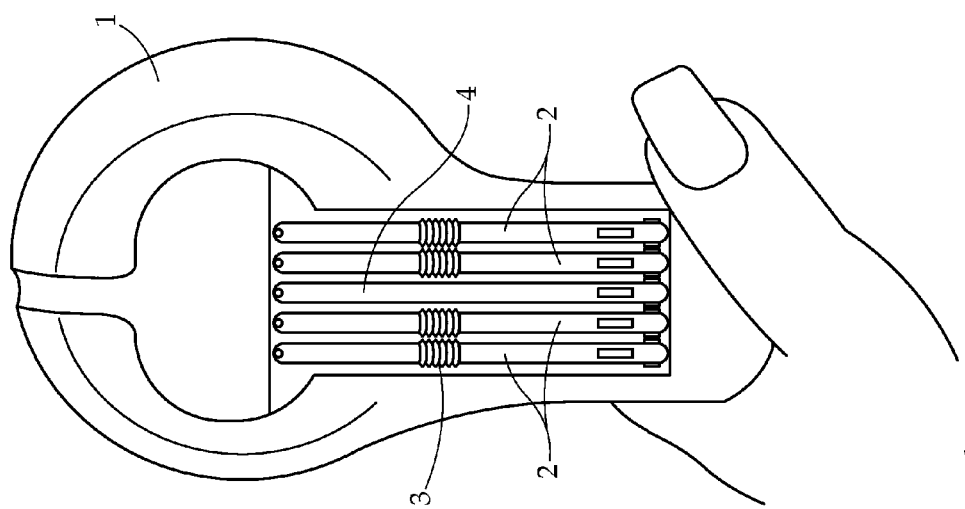
FIG. 1 is a backside view of the inside of invention exposing the grout and tile cleaner and multi-functional hygienic water tools.
Figure 3:
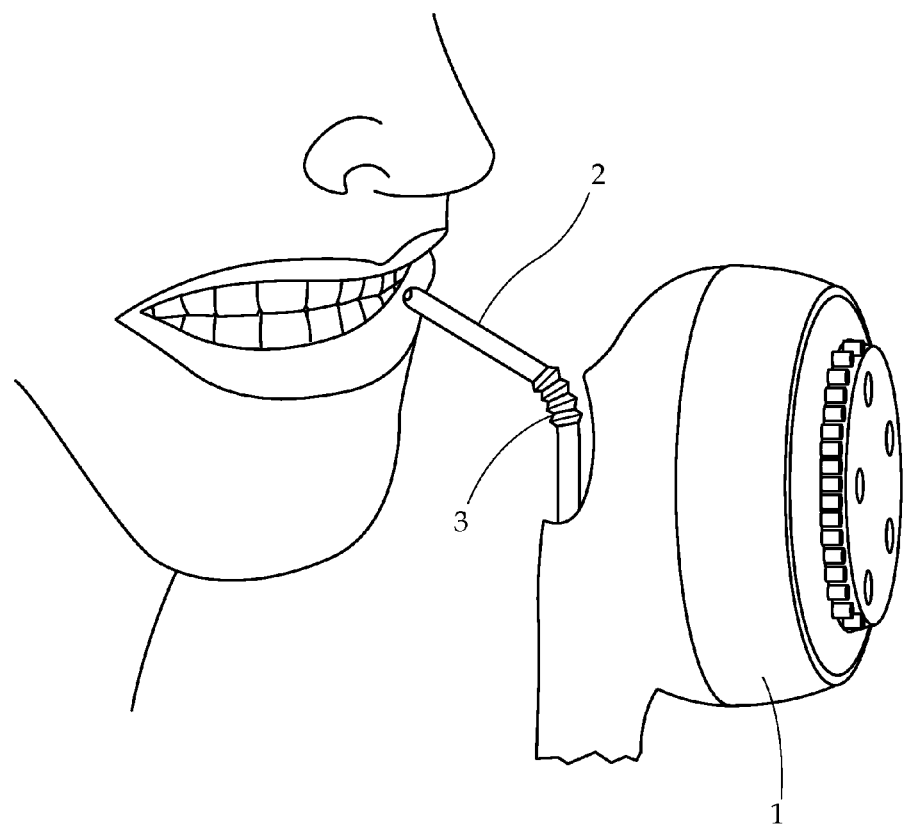
FIG. 3 is a right side view of the invention in a state removed from its wall-mounted plumbing.

The detailed description set forth below is intended as a description of presently preferred embodiments of the invention and does not represent the only forms in which the instant invention may be construed and/or utilized. The description sets forth the functions and a sequence of steps for producing the system and accompanying apparatus. However, it is to be understood that the same or equivalent functions and sequences may be accomplished by different embodiments and are also intended to be encompassed within the scope of the invention.

FIGS. 1-5 depict various viewpoints of the present apparatus and its components which includes a showerhead 1 which is easily and quickly removed from its wall-mounted plumbing, multi-functional hygienic water tools 2 for maintaining proper oral hygiene through the washing of the teeth and ears, and a tile and grout cleaner 4 for an efficient and easy way to clean the shower.

The multi-functional hygienic water tools 2 are comprised of flexible tubing 3 so that the hygienic water tools 2 can be bent at various angles away from the showerhead 1, enabling the user to place the multi-functional hygienic water tools 2 to the desired position.

The showerhead 1 is comprised of sliding mechanisms 5 for each of the multi-functional hygienic water tools 2 and the tile and grout cleaner 4. When one of the sliding mechanisms 5 are engaged and snapped into place, it will cause water to flow from the showerhead 1 to whatever multi-functional hygienic water tool 2 or tile and grout cleaner 4 is being used. The sliders 5 are made with a curved designed to be easily engaged with the use of a human thumb. The sliders 5 can be colored or numbered with braille so that anyone can easily identify the desired multi-functional hygienic water tool 2.

Each of the multi-functional hygienic water tools 2 and the tile and grout cleaner 4 will have their own individual compartments 12 to keep the multi-functional hygienic water tools 2 from being exposed to germs. The inside of the compartments 12 and inside of the multi-functional hygienic water tools 2 will also have an antibacterial coating for added germ protection.

The multi-functional hygienic water tools 2 will come up through a small hole 18, at the top of each of the individual compartments 12, and cover 19. The sliding mechanisms 5, will be moved with a spring action 15 that is rubberized. At the bottom of the multi-functional hygienic water tools 2 and tile and grout cleaner 4 compartment 12 in base of handle, there will be a small hole 13 for drainage of water that may be on the multi-functional hygienic water tools 2 when not in use.

FIGS. 5-8 depict various viewpoints of another embodiment of the device. In this embodiment, the showerhead 1 is comprised of one water-flow pulsator to which multi-functional hygienic water tools 7 and the tile and grout cleaner 8 can be attached to. The showerhead 1 has detaching personal multi-functional hygienic water tools which are made from antibacterial/mold resistant material. The multi-functional hygienic water tools 7 also have a bending mechanism 9, so that it may be bent into various angles for easy use.

The second embodiment also comes with five multifunctional hygienic water tools 7 of difference colors and each are marked with braille color name.

FIG. 8 depicts the antibacterial storage device where the multi-functional hygienic water tools 7 are held. This storage device 10 also holds the tile and grout cleaning attachment 8.

Figure 5:
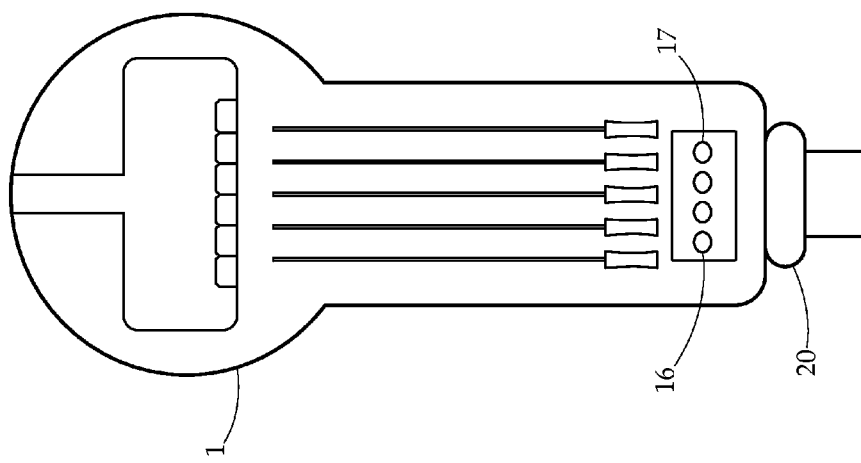
FIG. 5 is a view of the control panel on the outside of the handle on the backside of the showerhead along with the twisting mechanism directly below the showerhead handle.
Figure 4:
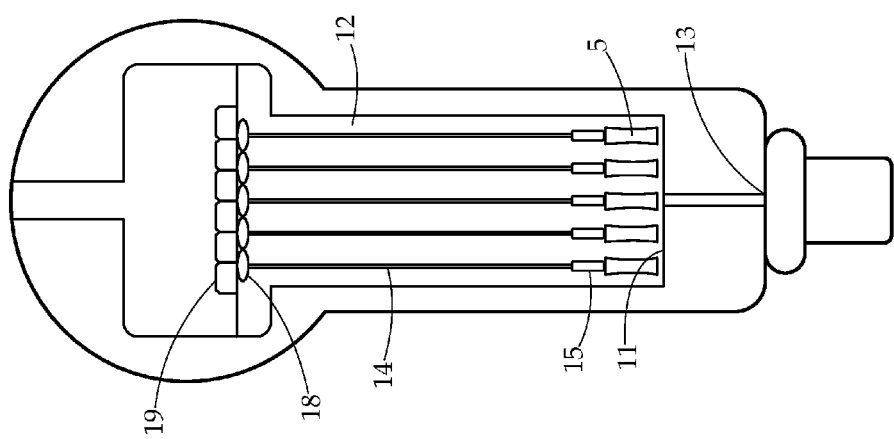
FIG. 4 is a view of the inside of the showerhead displaying the separate chamber compartments and the spring-activated rubber slides.

FIG. 5 depicts the control panel for these embodiments. On the handle of the showerhead 1 are controls 16 for water pressure and 17 pulsation. FIG. 5 also depicts the twisting mechanism 18 for these embodiments. It is located directly below the showerhead 1 handle such that, when engaged and twisted, the water flow is shifted from the front of the showerhead 1 to the back 1.

The instant system also comprises a removably attachable and detachable embodiment wherein the user is afforded the capability to install the instant system, including the control panel, the multi-functional hygienic water tools and tile/grout cleaner, and subsequently seamlessly detach the system from the installation point for storage or travel. The system may be configured to attach to existing piping, and particularly shower fittings, tub fittings, sink fittings and basin spigot fittings.

There has been outlined, rather broadly, the more important features of the versatile multi-purpose showerhead and water hygiene system in order that the detailed description that follows may be better understood, and its contribution to the art better appreciated. There are additional features of the system that will be described hereinafter and which will form the subject matter of the claims appended hereto.

In this respect, before explaining at least one embodiment of the system in detail, it is to be understood that the system is not limited in its application to the details of construction and to the arrangements of the components set forth in the following description or illustrated in the drawings. The system is capable of other embodiments and of being practiced and carried out in various ways that are not described herein. Also, it is to be understood that the phraseology and terminology employed herein are for the purpose of description and should not be regarded as limiting.

These together with other objects of the system, along with the various features of novelty, which characterize the system, are pointed out with particularity in the claims annexed to and forming a part of this disclosure. For a better understanding of the system, its operating advantages and the specific objects attained by its uses, reference should be made to the accompanying drawings and descriptive matter in which there are illustrations of the preferred embodiments of the device.

What is claimed is:

1. A multi-purpose showerhead system comprising:
    a handheld showerhead comprising:
        a handle mechanism;
        a showerhead portion integrally formed with the handle mechanism, wherein the showerhead portion includes a front area for dispensing shower water and a rear area opposite the front area;
        a water flow pulsator mechanism;
        an attachment mechanism located on the rear area of the showerhead portion and in fluid communication with the water flow pulsator mechanism; and
        a set of controls located on the handle mechanism;
    the multi-purpose showerhead system further comprising:
        a set of five multi-functional hygienic water tools;
        a tile and grout cleaning apparatus; and
        a storage device, wherein each of the water tools and the tile and grout cleaning apparatus are interchangeably attachable to the attachment mechanism of the showerhead, and wherein the water tools and the tile and grout cleaning apparatus are each configured for removable storage in the storage device when not attached to the attachment mechanism.

2. The multi-purpose showerhead system of claim 1, further comprising:
    a diverter mechanism connected to the handle mechanism of the handheld showerhead, wherein the diverter mechanism is configured to shift a volume of water flow from the front area of the showerhead portion to the rear area of the showerhead portion.

3. The multi-purpose showerhead system of claim 1, wherein:
    each of the multi-functional hygienic water tools are made from an antibacterial/mold-resistant material and are marked with an identifying braille inscription; and
    each of the multi-functional hygienic water tools are configured as flossing devices and include a deflection mechanism which allows for bending of the flossing devices in a range from zero degrees to 180 degrees.

* * * * *